__United States Patent__ [19]

Wudl

[11] Patent Number: 4,462,938
[45] Date of Patent: Jul. 31, 1984

[54] PROCESS FOR PRODUCING CHALCOGEN CONTAINING COMPOUNDS

[75] Inventor: Fred Wudl, Far Hills, N.J.

[73] Assignee: AT & T Bell Laboratories, Murray Hill, N.J.

[21] Appl. No.: 149,993

[22] Filed: May 15, 1980

[51] Int. Cl.$^3$ .................. C07C 155/04; C07C 163/00; C07D 421/04; C07D 409/04

[52] U.S. Cl. ............................... 260/550; 260/239 R; 549/39; 544/75

[58] Field of Search .............. 260/239 R, 550; 564/75

[56] References Cited

U.S. PATENT DOCUMENTS 2,888,445  5/1959  Hardman ............................ 564/75

OTHER PUBLICATIONS

Bechgaard et al. J. Org. Chem., vol. 40, No. 6, (1975), pp. 746-749.

Barnard et al., J. Chem Soc. pp. 2922-2926, (1961).
Rosenbaum et al., J. for Prakt. Chemie, 19, pp. 1-13, (1963).
Eilingfeld et al, Angew Chem., 73, pp. 836-845, (1960).

*Primary Examiner*—Paul M. Coughlan, Jr.
*Assistant Examiner*—D. B. Springer
*Attorney, Agent, or Firm*—Bruce S. Schneider

[57] ABSTRACT

Phosgene iminium chloride has been used as a reagent in a variety of reactions to produce compounds useful in the preparation of organic conductors, inorganic complexes, and heterocyclic compounds. This reagent undergoes expedient reactions with either $H_2Se$ or $H_2S$. Of particular interest is a synthetic process beginning with the production of dichalcogen carbamate by the reaction of phosgene iminium chloride with, for example, $H_2Se$ followed by subsequent processing steps to produce tetramethyl tetraselenafulvalene.

9 Claims, 2 Drawing Figures

PROCESS FOR PRODUCING CHALCOGEN CONTAINING COMPOUNDS

BACKGROUND OF THE INVENTION

1. Field of the Invention

This invention relates to chemical synthesis and, more particularly, to chemical synthesis involving chalcogens.

2. Art Background

The use of Se and S in organic and inorganic chemistry has been investigated for many years. However, interest has intensified particularly in organic Se and S chemistry since various heterocyclic compounds containing these elements have shown unusual properties such as high electronic conductivity useful for a variety of applications such as the production of high field magnets. For example, the discovery that tetramethyl tetraselenafulvalene is a superconductor at temperatures of approximately 0.9 degrees K. and pressures of approximately 12 Kbar has generated a great deal of excitement.

The synthesis of chalcogen, and particularly of Se containing compounds such as tetramethyl tetraselenafulvalene, however, often relies on the reactions of extremely undesirable materials such as carbon diselenide. Unfortunately, this reagent is both necessary for producing C=Se bonds (through the production of dichalcogen carbamate), and also particularly inappropriate for most commercial synthetic processes. Carbon diselenide, in fact, has several disadvantageous properties. For example, its odor is among the most noxious of all commonly used reagents. This undesirable property is compounded by its high density that makes typical fumehoods ineffective for removing its vapors from the atmosphere. This problem discourages its use in industry for synthetic processes. Additionally, its odor makes commercial synthesis unacceptable to the communities where production plants might be located.

Even if carbon diselenide were odorless, it would not be particularly suitable for large scale production and distribution. Carbon diselenide is usually produced by reaction of methylene chloride with Se at elevated temperatures. This reaction produces carbon diselenide in quite limited yields and further produces a host of other noxious chemicals. Thus, its production is expensive and presents additional toxicity problems. Further, carbon diselenide has a tendency to decompose and, therefore, does not transport or store well.

As a result of these problems the use of carbon diselenide has been limited to laboratory preparation where it is feasible to produce the reagent in situ and where environmental considerations are not as significant. These restrictions have limited the preparation of useful inorgano and organo selenium compounds and, in particular, has limited the preparation of Se heterocyclic compounds.

SUMMARY OF THE INVENTION

The synthesis of dichalcogen carbamate and, thus, in one embodiment, the production of C=Se bonds for use in both organic and inorganic synthesis is achieved without the use of carbon diselenide. The manufacture of the desired chalcogenide compound relies on the reactions of N, N disubstituted immonium dichlorocarbonyl salts (I),

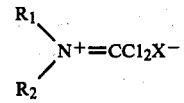

such as N, N dimethyl immonium dichlorocarbonyl chlorides (phosgene iminium chloride). For example, $H_2S$ or $H_2Se$ reacts with compounds of type I to form dichalcogen carbamates,

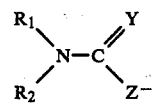

where Z and Y=Se or S. Compounds within the class represented by formula II are then useful in the production of Se or S heterocycles such as tetramethyl tetraselenafulvalene and in production of inorganic Se or sulfur complexes.

The reaction to form the desired Se=C (or S=C) bond is performed with chemicals that are easily removed in typical fumehoods, that are easily stored in gas cylinders, and that are commercially available for nominal cost.

DETAILED DESCRIPTION

Figure 1:
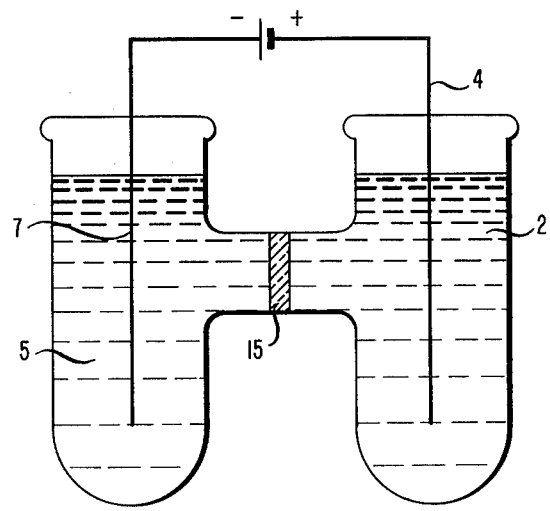
FIG. 1 is illustrative of an apparatus useful for producing crystals of conducting compounds containing chalcogens.

The subject invention depends on the reaction of N, N disubstituted immonium dichlorocarbonyl salts such as phosgene iminium chloride with chalcogen containing nucleophiles such as $H_2Se$ or $H_2S$. The overall reaction, for example, in the case of $H_2Se$ is represented by the equation,

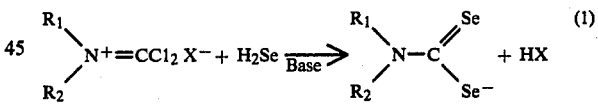

(It should be noted that the above reaction is equally useful when nucleophiles involving sulfur or a mixture of sulfur and selenium containing nucleophiles are employed. Although the primary interest in this reaction involves the selenides, the corresponding sulfides and mixed sulfides/selenides were Y and Z in II are S and Se respectively are also producible and are contemplated within the invention.) In reaction 1, the group used as $R_1$ and $R_2$ is not critical. These groups generally have no affect on the reaction. However groups such as tertiary butyl introducing severe steric hindrance should be avoided. Typical constituents for $R_1$ and $R_2$ are hydrocarbon residues. Additionally, the anion, $X^-$, of the N, N disubstituted ammonium dichlorocarbonyl salt is not critical. For example, anions such as $Cl^-$ and $Br^-$ are acceptable.

Compound II has a tendency to decompose in the presence of acids. To avoid this decomposition and the resulting degradation in yield, it is desirable to include in the reaction mixture a mild non-nucleophilic base such as a tertiary amine and, in particular, triethyl amine. These bases react with and remove excess acid before this acid can react with compound II. In a preferred embodiment it is desirable to introduce the nucleophile, H₂S or H₂Se, as the product of the nucleophile and a portion of the non-nucleophilic base. This produces a buffer solution that further controls pH. Additionally, a suitable solvent is utilized to dissolve the reactant of reaction 1, i.e., compound I and to dissolve the evolving product, i.e., compound II. It is possible to employ a solvent that solubilizes only compound I in some situations, e.g., if the product compound (compound II) is to be collected without further reaction. However, in many circumstances, compound II is used only as an intermediate and, thus, as a matter of convenience is kept in solution. Typical solvents useful for the purposes of reaction 1 are chlorinated hydrocarbons such as methylene chloride.

The reaction (1) is extremely exothermic. In order to appropriately control the reaction, it is desirable that it be performed at reduced temperatures. For most purposes, adequate control is achieved at temperatures of about or below −30 degrees C. The reactant (compound I) is moisture sensitive and the product (compound II) is oxygen sensitive, i.e., it polymerizes in the presence of oxygen. Thus to avoid undesirable side reactions, it is advantageous to perform reaction 1 under anaerobic conditions. This is conventionally done by maintaining a nitrogen atmosphere over the reaction mass. However, it is equally possible to use other inert atmospheres such as argon.

Once the compound of formula II is produced, it is either collected or used in further reactions. In the former case, an expedient method of collecting the compound is to evaporate the solvent used in reaction 1, to dissolve the residue in distilled deoxygenated water containing sodium bicarbonate, and then to precipitate the desired product by addition of a large cation such as tetrabutyl ammonium. Where further reaction is contemplated, the reaction mass is typically used without additional processing. For example, the product of reaction 1 is used to produce tetrasubstituted tetrachalcogenfulvalene, e.g., tetramethyl tetraselenafulvalene, using a portion of the synthetic procedure described in K. Bechgaard et al, *Journal of Organic Chemistry*, 40 746 (1975). The relevant portion described in the Bechgaard paper, starts at the point in the synthetic process where compound II is reacted with a haloketone. (It should be noted that the substituents on the haloketones R₃ and R₄, below, are not critical and any group which does not sterically interfere with the reaction is acceptable. Additionally, it is possible to use either chlorine or bromine as the halide, X, constituent of the haloketone.) A typical reaction sequence is,

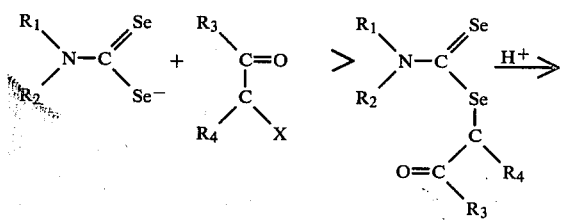

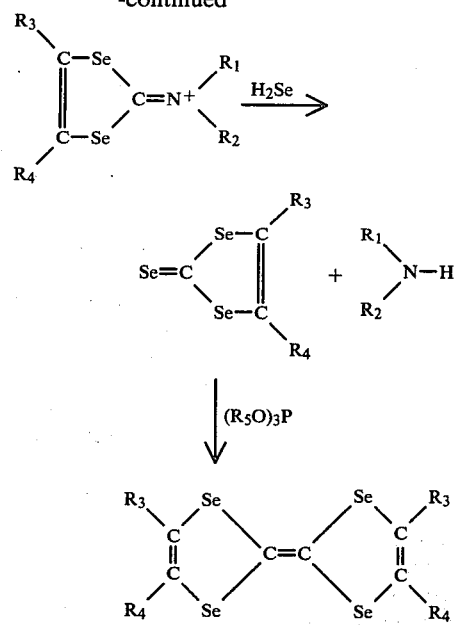

where R₅ is a hydrocarbon residue such as methyl.

As previously discussed the compounds having Se/-carbon bonds produced by the subject process are useful in devices that utilize their conductive properties. For example, devices relying on these conductivity properties are produced by attaching electrodes to the crystal and inducing current to pass between the electrodes through the crystal.

The following examples are illustrative of the reaction conditions used in the subject invention.

EXAMPLE 1

Approximately 8.6 ml of triethylamine was added to 75 ml of chloroform that had previously been dried with alumina. The solution was degassed by bubbling argon through it for approximately 15 minutes and then the solution was cooled to −10 degrees C. Hydrogen selenide was bubbled through the solution until all the triethylamine had reacted with it. (The consumption of all the triethylamine is detected by monitoring the pH of the solution. When the solution becomes neutral or slightly acidic the reaction is completed.)

The solution was purged with dry nitrogen to remove any excess H₂Se. Stirring of the solution was initiated. Then 5 grams of phosgene iminium chloride (as purchased from Aldrich Chemical Co.) and 8.6 ml of triethylamine were added in one aliquot. The phosgene iminium chloride dissolved slowly while the reaction mixture turned to an intense yellow-orange color. The solution was stirred for approximately 2 hours after addition of these reagents. This reaction yielded the desired Se compound, i.e., triethyl ammonium dimethyl diselenocarbamate.

The Se compound was then further reacted at −10 degrees C. by addition to the reaction mass of 0.062 moles of 3-bromo-2-butanone in 50 ml of alumina dried chloroform. This mixture was added dropwise while the solution was stirred. Stirring was continued for ½ hour at −10 degrees C. and then for 2 additional hours at room temperature. After the reaction, a small amount of precipitate was observed and this precipitate was removed by filtration. The solvent was then evaporated under vacuum, and the residue was washed with ether. The ether was removed in vacuo to yield a yellow solid (8.6 grams, 97 percent yield). This yellow solid product from the reaction of a haloketone and diselenium carbamate was then reacted in a series of steps as described in Bechgaard et al supra. An NMR spectrum was taken and this spectrum appeared to be identical to that described by Bechgaard et al, for tetramethyl tetraselenafulvalene.

EXAMPLE 2

The same procedure was followed except H$_2$S instead of H$_2$Se gas was utilized. The corresponding compound with the Se replaced by sulfur was obtained.

EXAMPLE 3

Figure 2:
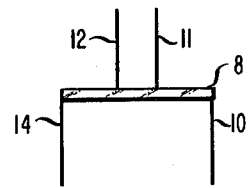
FIG. 2 is illustrative of an apparatus utilizing conductive compounds containing chalcogens.

Sixty milligrams of the tetramethyl tetraselenafulvalene produced in Example 1 was dissolved in 50 ml of chlorobenzene. This solution was placed in compartment 2 (FIG. 1) of an H cell having a medium porosity frit, 15. A platinum electrode 4 was then inserted in this solution. Compartment 5 of the apparatus was filled with chlorobenzene solvent and then a supporting electrolyte, tetrabutylammonium hexafluorophosphate, was added both to compartment 5 and to compartment 2. Sufficient quantities of this supporting electrolyte was added to these compartments to make the solute concentration of these compartments approximately 0.1 molar. A platinum electrode 7 was then inserted into the solution of compartment 5. A voltage of 0.4 V was applied with the positive electrode being electrode 4. The voltage was maintained until crystals having a size of approximately 1 centimeter by several tenths of a millimeter were obtained. (This took approximately 1 week.) The crystals grown were removed from electrode 4 and the largest crystal was chosen. Four electrodes, 10, 11, 12 and 14 were attached to the crystal, 8, as shown in FIG. 2. These electrodes were attached utilizing a gold conducting adhesive. A current of 100 microamps was applied across electrodes 10 and 14 and a voltage of 20 microvolts was measured between electrodes 11 and 12. (This value corresponds to a crystal 5 mm in length with a cross-sectional area of approximately 0.4 mm$^2$ and with a space of 2 mm between electrodes 11 and 12.)

I claim:

1. In a process for the synthesis of tetraselenafulvalenes comprising the steps of performing a series of reactions utilizing a diselenocarbamate as a reactant to ultimately form said tetraselenafulvalene, the improvement comprising the synthesis of said diselenocarbamate through the reaction of a reactant represented by the formula

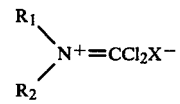

with the selenium containing entity produced by the combination of hydrogen selenide with a mild non-nucleophilic base wherein R$_1$ and R$_2$ are hydrocarbon residues which are sufficiently small that prevention of said reaction through steric hindrance is substantially avoided and wherein X$^-$ comprises an anion.

2. The process of claim 1 wherein said N, N disubstituted immonium dichlorocarbonyl salt is chosen from the group consisting of chloride and bromide salts.

3. The process of claim 1 wherein said hydrocarbon residues are methyl groups.

4. The process of claim 1 wherein said tetrasubstituted tetraselenafulvalene is tetramethyl tetraselenafulvalene.

5. The process of claim 1 wherein said mild non-nucleophilic base comprises a tertiary amine.

6. The process of claim 5 wherein said tertiary amine comprises triethyl amine.

7. A process for producing a compound represented by the formula

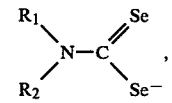

the improvement comprising producing said compound by reaction of a reactant represented by the formula

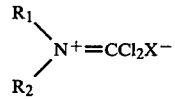

with the selenium containing entity produced by the combination of hydrogen selenide with a mild non-nucleophilic base wherein R$_1$ and R$_2$ are hydrocarbon residues which are sufficiently small that prevention of said reaction through steric hindrance is substantially avoided and wherein X$^-$ comprises an anion.

8. The process of claim 7 wherein said mild non-nucleophilic base comprises a tertiary amine.

9. The process of claim 8 wherein said tertiary amine comprises triethyl amine.

* * * * *